(12) United States Patent
Jiang et al.

(10) Patent No.: US 8,436,297 B2
(45) Date of Patent: *May 7, 2013

(54) SYSTEM AND METHOD FOR DIVERSION OF A LIQUID CHROMATOGRAPHY ELUANT

(75) Inventors: Tongbo Jiang, Bedford, MA (US); Cheryl Follo, Billerica, MA (US); Maurice G. Phelan, Swampscott, MA (US)

(73) Assignee: EMD Millipore Corporation, Billerica, MA (US)

( * ) Notice: Subject to any disclaimer, the term of this patent is extended or adjusted under 35 U.S.C. 154(b) by 98 days.

This patent is subject to a terminal disclaimer.

(21) Appl. No.: 12/674,870

(22) PCT Filed: Aug. 22, 2008

(86) PCT No.: PCT/US2008/010027
§ 371 (c)(1), (2), (4) Date: Feb. 23, 2010

(87) PCT Pub. No.: WO2009/029232
PCT Pub. Date: Mar. 5, 2009

(65) Prior Publication Data
US 2011/0114833 A1    May 19, 2011

Related U.S. Application Data

(60) Provisional application No. 60/966,116, filed on Aug. 24, 2007.

(51) Int. Cl.
*H01J 49/00* (2006.01)
(52) U.S. Cl.
USPC .......................... 250/282; 210/659

(58) Field of Classification Search ........... 250/282, 250/288; 73/61.56; 210/659; 137/625.46
See application file for complete search history.

(56) References Cited

U.S. PATENT DOCUMENTS 4,891,137 A * 1/1990 Nohl et al. ............ 210/644
4,962,042 A * 10/1990 Morabito et al. ......... 436/161
(Continued)

FOREIGN PATENT DOCUMENTS
WO    WO 99/16945         4/1999
WO    WO 2009/029231 A2   3/2009
WO    WO 2009/029231 A3   3/2009

OTHER PUBLICATIONS

Jenke, R. et al., Extractable/leachables from plastic tubing used in product manufacturing, International Journal of Pharmaceutics, 315 (1-2): 75-92(2006).*

(Continued)

*Primary Examiner* — David A Vanore
*Assistant Examiner* — Wyatt Stoffa
(74) *Attorney, Agent, or Firm* — Hamilton, Brook, Smith & Reynolds, P.C.

(57) ABSTRACT

In accordance with an embodiment of the invention, there is provided a method for reducing or eliminating matrix interfering components in a biopharmaceutical product in a liquid chromatography-mass spectrometry system. The method comprises diverting to waste the entire flow of an eluant emerging from liquid chromatography of a sample, for a time period to remove contaminants that cause matrix interference to a degree sufficient to allow a desired accuracy in detection of an extractable; and, after the time period, directing the entire flow of the eluant to a mass spectrometer to detect the presence of the extractable.

9 Claims, 6 Drawing Sheets

U.S. PATENT DOCUMENTS

| | | | | |
|---|---|---|---|---|
| 5,468,643 | A | * | 11/1995 | Su et al. ............... 436/161 |
| 5,703,360 | A | * | 12/1997 | Fischer et al. ............... 250/288 |
| 5,827,830 | A | * | 10/1998 | Nudelman et al. ............... 514/25 |
| 6,641,783 | B1 | | 11/2003 | Pidgeon et al. |
| 7,220,383 | B2 | | 5/2007 | Anderson et al. |
| 7,834,313 | B2 | * | 11/2010 | Bystrom et al. ............... 250/282 |
| 8,212,207 | B2 | | 7/2012 | Jiang et al. |
| 2005/0036917 | A1 | * | 2/2005 | Anderson et al. ............... 422/99 |
| 2005/0194318 | A1 | * | 9/2005 | Ozbal et al. ............... 210/656 |
| 2006/0133964 | A1 | * | 6/2006 | Bailey et al. ............... 422/99 |
| 2007/0048187 | A1 | * | 3/2007 | Sheehan ............... 422/89 |
| 2007/0251302 | A1 | * | 11/2007 | Iwata ............... 73/61.56 |
| 2008/0257019 | A1 | * | 10/2008 | Rosati et al. ............... 73/61.55 |
| 2009/0050212 | A1 | * | 2/2009 | Dourdeville et al. ............... 137/14 |
| 2010/0015652 | A1 | * | 1/2010 | Granda et al. ............... 435/23 |
| 2010/0024527 | A1 | * | 2/2010 | Lamarr et al. ............... 73/61.56 |
| 2010/0107742 | A1 | * | 5/2010 | Liu et al. ............... 73/61.56 |
| 2010/0219338 | A1 | * | 9/2010 | Bystrom et al. ............... 250/282 |
| 2010/0282962 | A1 | * | 11/2010 | Machuron-Mandard et al. ............... 250/282 |
| 2011/0114833 | A1 | * | 5/2011 | Jiang et al. ............... 250/282 |
| 2011/0278446 | A1 | | 11/2011 | Jiang et al. |

OTHER PUBLICATIONS

Colton, R. H., et al., "Extractables and Leachables Evaluations for Filters", *The World's Knowledge*, Chapter 14: 389-411 (Jan. 1, 2008).

Notification of Transmittal of the International Search Report and Written Opinion of the International Searching Authority from counterpart International Application No. PCT/US2008/010027, dated Dec. 5, 2008.

Notification of Transmittal of the International Search Report and Written Opinion of the International Searching Authority from counterpart International Application No. PCT/US2008/010026, dated Apr. 23, 2009.

Colton, R. H., et al., "Extractables and Leachables Evaluations for Filters", *The World's Knowledge*, Chapter 14: 389-411.

Fichtner, S., et al., "Determination of "Extractables" on Polymer Materials by Means of HPLC-MS", *Journal of Pharmaceutical Science and Technology*, 60(5): 291-301 (Sep. 2006).

Jenke, D., et al., "The effect of solvent polarity on the accumulation of leachables from pharmaceutical product containers," *European Journal of Pharmaceutical Sciences*, 27(2-3): 133-142 (2006).

Jenke, D., R., et al., "Extractables/leachables from plastic tubing used in product manufacturing", *International Journal of Pharmaceutics*, 315(1-2): 75-92 (2006).

Jiang, T., et al., "Extractables$^a$ from Filter Components in Model Solvent Streams for Pharmaceutical Filtration Processes", *PDA Journal of Pharmaceutical Sciences and Technologies*; 57(4): 287-299 (Aug. 2003).

Kao, Y-H., et al., "Characterization of Filter Extractables by Proton NMR Spectroscopy: Studies on Intact Filters with Process Buffers"*Journal of Pharmaceutical Science and Technology*, 55(5): 268-277 (2001).

Reif, O. W., et al., "Analysis and Evaluation of Filter Cartridge Extactables for Validation in Pharmaceutical Downstream Processing", *PDA Journal of Pharmaceutical Sciences and Technologies*; 50(6): 399-410 (1996).

Stone, T. E., et al., "Methodolgy for Analysis of Filter Extractables: A Model Stream Approach", *Pharmaceutical Technology*, 116-130 (Oct. 1994).

Stone, T. E., et al., "The Model Stream Approach: Defining the Worst-Case Conditions", *Pharmaceutical Technology*, pp. 34-51 (Feb. 1996).

Sun, Li, et al., "The effect of β-cyclodextrin on liquid chromatography/electrospray-mass spectrometry analysis of hydrophobic drug molecules", *Journal of Chromatography A*, 1161: 261-268 (2007).

Weltzmann, C. J., "The Use of Model Solvents for Evaluation Extractables from Filters Used to Process Pharmaceutical Product", *Pharmaceutical Technology*, pp. 73-99 (Apr. 1997).

Notification Concerning Transmittal of International Preliminary Report on Patentability (Chapter I of the Patent Cooperation Treaty) from counterpart International Application No. PCT/US2008/010026, Dated: Mar. 4, 2010.

Notification Concerning Transmittal of International Preliminary Report on Patentability (Chapter I of the Patent Cooperation Treaty) from counterpart International Application No. PCT/US2008/010027, Dated: Mar. 4, 2010.

U.S. National Stage Application PCT/US2008/010026, assigned U.S. Appl. No. 12/674,874, with an International Filing Date of Aug. 22, 2008.

Extended European Search Report for counterpart European Application No. 12175163.0-2204, "System and Method for Diversion of a Liquid Chromatography Eluant", dated Sep. 7, 2012.

Notice of Allowance dated Mar. 1, 2012 from U.S. Appl. No. 12/674,874.

English translation of Japanese Office Action for counterpart Japanese Application No. 2010-521891, "System and Method for Diversion of a Liquid Chromatography Eluan," dated Oct. 15, 2012, which references the following: WO 2004/0423874 A1, May 21, 2004, Varian Inc. (corresponds to JP 2006-504972); Sun, Li, et al., "The effect of β-cyclodextrin on liquid chromatography/electrospray-mass spectrometry analysis of hydrophobic drug molecules", Journal of Chromatography A, 1161: 261-268 (2007); and U.S. Patent No. 5,703,360, Dec. 30, 1997, Fischer, et al.

* cited by examiner

SYSTEM AND METHOD FOR DIVERSION OF A LIQUID CHROMATOGRAPHY ELUANT

RELATED APPLICATION

This application is the U.S. National Stage of International Application No. PCT/US2008/010027, filed Aug. 22, 2008, which designates the U.S., published in English, and claims the benefit of U.S. Provisional Application No, 60/966,116, filed Aug. 24, 2007. The entire teachings are incorporated by reference herein.

BACKGROUND OF THE INVENTION

Filter devices are extensively used to remove particles and microorganisms or purify proteins from biopharmaceutical products. During filtration, materials from a filter device could be extracted into a product and affect its efficacy and safety. The FDA requires the evaluation of filter extractables for both human and animal drug products.

The filter extractables are complex mixtures consisting primarily of low concentrations of oligomers and additives of diverse physical and chemical properties. Since the concentration of other components of the biopharmaceutical product will be higher, the analytical signal for the filter extractables can be masked, and therefore rendering their presence undetectable. Conventionally, the Model Stream Approach (Stone, T. E.; Goel, V.; Leszczak, *J. Pharmaceutical Tech.* 1994, 116-130) is used to study the extractables present following the filtration step. During this method, the filter device is subjected to a model solvent that simulates specific chemical effects of a pharmaceutical solution. Under this principle, the model solvents are selected to represent the extremes in environment (high or low pH, high salt concentrations, or organic solvents) to which the filter device may be exposed, but not to be identical to the actual contents of the biopharmaceutical product. A "worst case scenario" can be created under aggressive conditions where the filter extractables content is maximized. Analytical techniques such as liquid chromatography UV detection (LCUV), gas chromatography mass spectrometry (GCMS) and Fourier transform infrared spectrometry (FTIR) are employed to detect the presence of extractables into the model solvent during the testing procedure.

SUMMARY OF THE INVENTION

In accordance with an embodiment of the invention, there is provided a method for reducing or eliminating matrix interfering components in a biopharmaceutical product in a liquid chromatography-mass spectrometry system. The method comprises diverting to waste the entire flow of an eluant emerging from liquid chromatography of a sample, for a time period to remove contaminants that cause matrix interference to a degree sufficient to allow a desired accuracy in detection of an extractable; and, after the time period, directing the entire flow of the eluant to a mass spectrometer to detect the presence of the extractable.

In further, related embodiments, the method may comprise directing flow of a calibrant liquid to the mass spectrometer during the time period; and may comprise directing flow of the calibrant liquid to waste after the time period. Diverting the eluant to waste during the time period and directing the eluant to the mass spectrometer after the time period may be performed using a six-port injection valve. The method may comprise directing the entire flow of the eluant to a port of the six-port injection valve that is adjacent to both (i) a port from which liquid flows directly to a mass spectrometer; and (ii) a port from which liquid flows directly to waste. Directing flow of the calibrant liquid to the mass spectrometer during the time period and directing flow of the calibrant liquid to waste after the time period may be performed using a six-port injection valve. The method may comprise directing flow of the calibrant liquid to the mass spectrometer during the time period by way of a flow loop between two adjacent ports of the six-port injection valve.

In accordance with another embodiment of the invention, there is provided a liquid chromatography diverter for reducing or eliminating matrix interfering components in a biopharmaceutical product in a liquid chromatography-mass spectrometry system. The liquid chromatography diverter comprises an eluant input port of a six-port injection valve, the eluant input port being in a liquid flow connection with a liquid chromatogaphy column; and a mass spectrometer output port of the six-port injection valve, the mass spectrometer output port being in a liquid flow connection with a mass spectrometer. The six-port injection valve is configured to be automatically switched between a waste flow configuration and a source flow configuration, the waste flow configuration diverting an entire flow from the eluant input port to be directed to waste, and the source flow configuration directing the entire flow from the eluant input port to be directed to the mass spectrometer.

In further, related embodiments, the mass spectrometer output port may be an adjacent port of the six-port injection valve to the eluant input port, and a waste port may be another adjacent port to the eluant input port. The waste flow configuration may direct the entire flow from the eluant input port to waste via the waste port, and the source flow configuration may direct the entire flow from the eluant input port to the mass spectrometer via the mass spectrometer output port. The liquid chromatography diverter may further comprise a calibrant flow loop between two adjacent ports of the six-port injection valve, the waste flow configuration directing flow of a calibrant liquid through the calibrant flow loop and to the mass spectrometer, and the source flow configuration directing flow of the calibrant liquid to waste and forming a closed flow loop that includes the calibrant flow loop.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows. The teachings of all patents, published applications and references cited herein are incorporated by reference in their entirety.

In accordance with an embodiment of the invention, there is provided a liquid chromatography diverter, and a method for diversion of a liquid resulting from liquid chromatography, that assists in reducing the presence of interfering compounds in a sample that is to be analyzed by mass spectrometry. Such an embodiment according to the invention allows a user to measure the amount of extractables in a drug or biopharmaceutical product, by reducing the presence of interfering compounds that could mask extractable peaks in the mass spectrometry analysis.

By way of illustration of the liquid chromatography diverter according to an embodiment of the invention, there is first described the use of a conventional injection valve in a similar context. Conventional injection valves can be switched between a "waste" setting and a "source" setting, which alter the liquid flow pattern between ports of the injection valve.

Figure 1A:
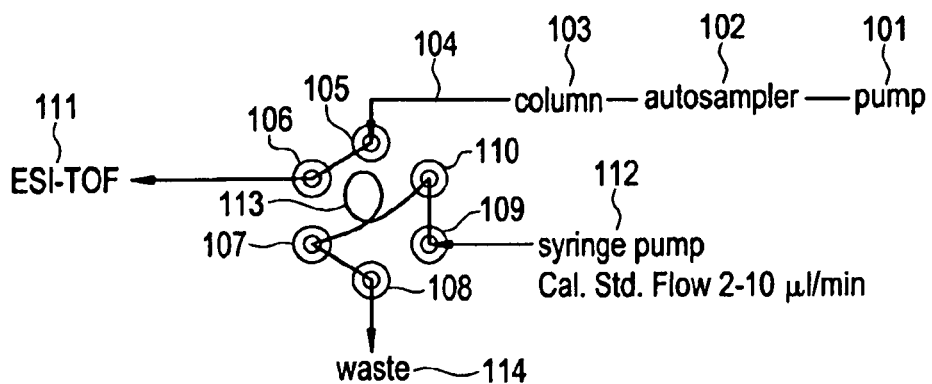
FIG. 1A is a schematic diagram of a liquid flow pattern when a conventional injection valve is used in a liquid chromatography/mass spectrometry technique, with the injection valve in the "waste" setting.

FIG. 1A is a schematic diagram of a liquid flow pattern when a conventional injection valve is used in a liquid chromatography/mass spectrometry technique, with the injection valve in the "waste" setting. Liquid to be analyzed flows from a pump 101 into an autosampler 102, and from there into a liquid chromatography column 103. After the liquid travels through the liquid chromatography column 103, liquid chromatography eluant 104 enters a first port 105 of a conventional six-port injection valve. The eluant 104 includes filter extractables, which are of interest for detection in the drug or biopharmaceutical product, as well as compounds that interfere with measurement of the extractables. With the conventional six-port injection valve in the "waste" setting, the eluant flows directly from the first port 105 to the second port 106 of the valve, and from there directly to the mass spectrometer 111. Meanwhile, a calibrant liquid flows from a syringe pump 112 to a fifth port (counting counter-clockwise around the six-port injection valve) 109 of the valve. The calibrant liquid then flows to a sixth port 110, and from there through a flow loop 113 that is positioned in series flow relationship between the sixth port 110 and a third port 107 of the six-port valve. From the third port 107, the calibrant liquid proceeds to a fourth port 108 and from there to waste 114.

Figure 1B:
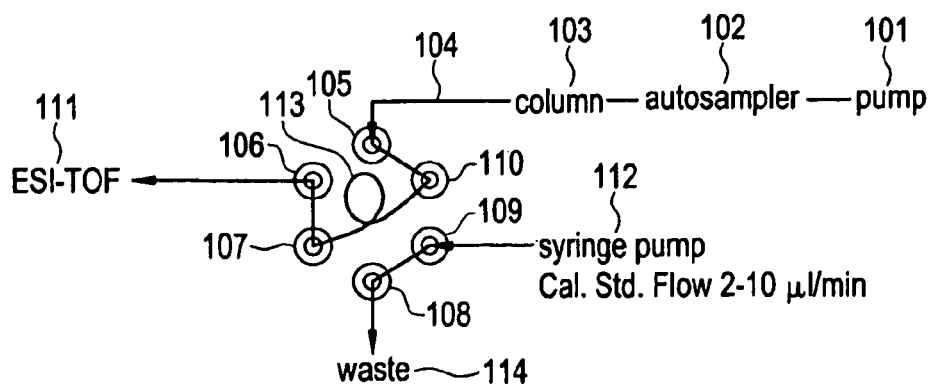
FIG. 1B is a schematic diagram of a liquid flow pattern when the conventional injection valve of FIG. 1A is switched to the "source" setting.

FIG. 1B is a schematic diagram of a liquid flow pattern when the conventional injection valve of FIG. 1A is switched to the "source" setting. As in FIG. 1A, liquid initially flows from the pump 101, to the autosampler 102, and through the liquid chromatography column 103 to produce the eluant 104, which is introduced into the first port 105. With the six-port valve in the "source" setting, the eluant 104 is then directed into the sixth port 110, and through the flow loop 113 to the third port 107. Because the flow loop 113 previously contained calibrant liquid in the "waste" setting of FIG. 1A, some calibrant liquid is swept along with the eluant as it flows through the flow loop 113. From the third port 107, the eluant then flows to the second port 106, and then directly to the mass spectrometer 111. Because some calibrant liquid is carried with the eluant, the calibrant liquid is introduced to the mass spectrometer 111 along with the eluant, to allow mass calibration. Meanwhile, the calibrant liquid coming from the syringe pump 112 is directed to the fifth port 109, and from there via the fourth port 108 to waste 114.

Using the conventional six-port injection valve as in FIGS. 1A and 1B, the valve can be switched via time segments in the acquisition method between the "waste" setting of FIG. 1A and the "source" setting of FIG. 1B. However, in both settings of the conventional six-port injection valve, the liquid chromatography eluant 104 is continuously introduced into the mass spectrometer 111, and therefore carries with it compounds that interfere with, or are incompatible with, the mass spectrometry analysis. It is therefore difficult to accurately detect and measure the presence of filter extractables in a drug sample using the conventional six-port injection valve of FIGS. 1A and 1B.

Figure 2A:
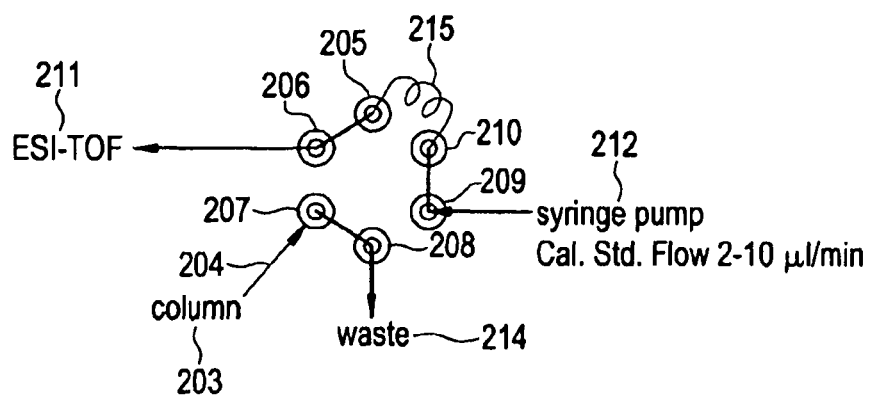
FIG. 2A is a schematic diagram of a liquid flow pattern through a liquid chromatography diverter according to an embodiment of the invention, with the diverter in the "waste" setting.

By contrast, FIG. 2A is a schematic diagram of a liquid flow pattern through a liquid chromatography diverter according to an embodiment of the invention, with the diverter in the "waste" setting. Unlike in the conventional six-port injection valve of FIGS. 1A and 1B, the diverter of FIGS. 2A and 2B includes a flow loop 215 between adjacent ports of a six-port injection valve, and introduces the liquid chromatography eluant 204 at a port 207 that is adjacent to both the port 206 that leads to the mass spectrometer 211 and the port 208 that leads to the waste 214. In the "waste" setting, calibrant liquid flows from the syringe pump 212 into the fifth port 209 of a six-port injection valve, and from there to the sixth port 210. Using the added flow loop 215 between the adjacent sixth port 210 and first port 205, the calibrant liquid then flows into the first port 205. From there, the calibrant liquid is directed to the second port 205, and to the mass spectrometer 211. Meanwhile, the eluant 204 from the liquid chromatography column 203 enters the diverter at the third port 207, and is directed to the fourth port 208, and from there is directed to waste 214. Therefore, in the "waste" setting, using the diverter of the embodiment of FIG. 2A, all of the eluant 204 from the liquid chromatography column flows to the waste 214. Thus, in the "waste" setting, all of the interfering compounds, which are present in the eluant 204, are likewise directed to waste 214 along with the eluant; while the mass spectrometer 211 is receiving calibrant liquid only.

Figure 2B:
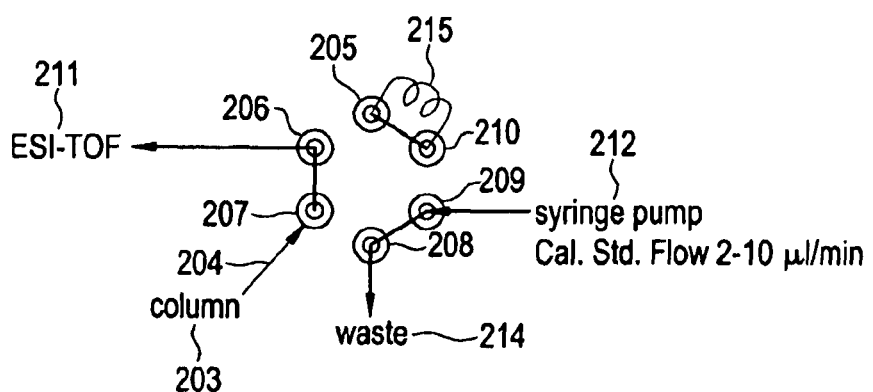
FIG. 2B is a schematic diagram of a liquid flow pattern through a liquid chromatography diverter according to an embodiment of the invention, with the diverter in the "source" setting.

FIG. 2B is a schematic diagram of a liquid flow pattern through a liquid chromatography diverter according to an embodiment of the invention, with the diverter in the "source" setting. Here, the eluant 204 emerging from the liquid chromatography column 203 enters the third port 207 and is directed to the second port 206, and from there is lead directly to the mass spectrometer 211, to allow analysis of filter exactrables in the eluant. The flow from the sixth port 210 to the first port 205 is made to form a closed loop with the flow loop 215, since the flow path between the first port 205 and second port 206 are closed off, as is the flow path between the fifth port 209 and sixth port 210. Meanwhile, the calibrant liquid flowing from the syringe pump 212 is directed from the fifth port 209 to the fourth port 208, and from there to waste 214.

Using the diverter of the embodiment of FIGS. 2A and 2B, the valve can be switched via time segments in the acquisition method between the "waste" setting of FIG. 2A and the "source" setting of FIG. 2B. However, unlike the technique using the conventional valve of FIGS. 1A and 1B, the embodiment of FIGS. 2A and 2B allows liquid chromatography eluant 204 to be directed entirely to waste, in the "waste" setting; and then to be directed entirely to the mass spectrometer, in the "source" setting. In this way, the diverter of FIGS. 2A and 2B may be switched to the "waste" setting for a time period, such as, for example, the first ten minutes of liquid chromatography eluant flow—during which time most or nearly all of the compounds are eluted that interfere with, or are incompatible with, mass spectrometry measurement of extractables. Then, once most or nearly all of the interfering compounds have been eluted and sent to waste, the diverter of FIGS. 2A and 2B may be switched to the "source" setting to allow the liquid chromatography eluant to flow directly to the mass spectrometer to allow measurement of extractables without interference from the interfering compounds. Thus, the liquid chromatography diverter of FIGS. 2A and 2B allows more accurate detection and measurement of the presence of extractables in a drug or biopharmaceutical sample.

In accordance with the embodiment of FIGS. 2A and 2B, the time period during which the diverter is in the "waste" mode and liquid chromatography eluant is sent directly to waste may be determined by analyzing the times at which most of the interfering compounds are eluted, by comparison with the times at which the extractables are eluted. For example, a mass spectrometry peak for the interfering compounds may be observed over a certain time period, followed by the appearance of a peak for the extractables. Ideally, the diverter should be switched from "waste" to "source" at the latest time possible before the first extractable compound characteristic of interest emerges in the liquid chromatography eluant. As noted above, ten minutes is one example of a useful time period for using the "waste" setting of the diverter, but other time periods may be used depending on the nature of the filter material, the extractable compounds, the interfering compounds, the protocol for the autoclave cycle used to sterilize the filter device, the contents of the drug or biopharmaceutical product, and other factors. Generally, the eluant should be diverted for a time period to remove the contaminants that cause matrix interference to a degree sufficient to allow a desired accuracy in detection of the extractable.

In accordance with an embodiment of the invention, the six-port injection valve used with the diverter of FIGS. 2A and 2B may, for example, be based on a six-port injection valve available from Bruker Daltonics Inc., Billerica, Mass., modified to add the flow loop 215 and use the flow pattern of an embodiment according to the invention. The calibrant liquid may, for example, flow at a rate of 2-10 microliters per minute. The mass spectrometer 211 may, for example, be a micrOTOF mass spectrometer system available from Broker Daltonics Inc., Billerica, Mass.

An embodiment according to the invention, in which the foregoing diverter may be used, is a technique for using liquid chromatography-mass spectrometry to detect the presence of extractables in a biopharmaceutical product, such as filter extractables introduced by filtration of a biopharmaceutical product or other extractables that may arise from product-contacting materials in the manufacturing and processing of the biopharmaceutical product, such as plastics. In contrast to current technology for testing extractables, the method disclosed herein can be used to detect the presence of filter and other extractables in the actual biopharmaceutical product, rather than using a model solvent system. Detection of filter and other extractables in the actual drug product provides an accurate characterization of the extractables profile likely to be introduced to the human or animal patient by the processed biopharmaceutical product.

One embodiment of this invention is a method of detecting extractables in a biopharmaceutical product by preparing a reference sample of a biopharmaceutical product absent of any extractables, to which an extractables standard is added. The reference sample is then separated by liquid chromatography (LC). Following the separation, the sample is diverted to waste for a period of time to remove components in the reference sample that cause matrix interference with the detection of the extractables. The remaining reference sample is processed through a mass spectrometer to obtain a reference mass spectrum. Similarly, a test sample is prepared. The test sample is the biopharmaceutical product that may contain extractables introduced by filtration of the biopharmaceutical product or by a manufacturing process thereof. Liquid chromatography is used to separate the test sample. Following the separation, the test sample is diverted to waste for a period of time to remove components in the test sample that cause matrix interference with the detection of the extractables. The remaining test sample is processed through a mass spectrometer to obtain a test mass spectrum. The test sample mass spectrum is compared to the reference sample mass spectrum to verify the presence or absence of the extractables in the test sample. In one embodiment, the extractables are filter extractables that are introduced by filtration of the biopharmaceutical product. In another embodiment, the extractables can be anything that may leach from equipment, materials or surfaces used to manufacture and process the biopharmaceutical product or intermediates, such as plastics. In a particularly preferred embodiment, the filter extractables can be from polypropylene (PP) support membranes or polyvinylidene fluoride (PVDF) microporous membranes (such as from commercially available filters and membranes under the name Durapore® (Millipore® Corporation)).

In another embodiment of the invention, the quantity of the extractables present in the biopharmaceutical product by LCMS can be determined.

Another embodiment of the invention is directed to a method of using liquid chromatography-mass spectrometry (LCMS) to detect filter extractables using characteristic retention times of filter extractables. A further embodiment is to use average retention times of about 11.5 and about 12.4 minutes.

Another embodiment of the invention is directed to a method of using liquid chromatography-mass spectrometry (LCMS) to detect characteristic ions of filter extractables. A further embodiment is to detect ions at about 329.2 and about 357.2 M/Z.

In another embodiment of the invention, the sample is separated by LC and then diverted to waste for a period of time before being processed by the MS. In another embodiment of the invention, the length of time the sample is diverted to waste following LC separation is dependent upon the type of filter used, the sterilization and filtration conditions, and the contents of the biopharmaceutical product. In another embodiment, the diversion should occur at the latest time possible before the first target extractables compound characteristic to the filter of interest is eluted from the LC step. In another embodiment of the invention, the period of time is up to 10 minutes. In another embodiment, the diversion to waste time is 10 minutes.

In another embodiment of the invention, components that cause matrix interference are selected from a group consisting of active pharmaceutical ingredients; buffering agents;

salts; preservatives; solubilizers; chelating agents; acids; bases; sugars; proteins, peptides, and combinations thereof.

The Food and Drug Administration (FDA) requires evaluation of filter extractables during the approval process for a drug intended for human or animal use. According to the FDA, the solvent used to extract the filter extractables from the filter device would ideally be the drug product itself, thus obtaining the same qualitative extraction profile (Guidance for Industry: "The Container Closure Systems for Packaging Human Drugs and Biologics." 1999; Attachment C: Extraction Studies). However, detection of the filter extractables is difficult to accomplish in the actual biopharmaceutical solution, largely because the concentration of the filter extractables in the filtered drug product is often orders of magnitude lower than that of other components of the solution. To circumvent this analytical obstacle, the current method for filter extractables detection is achieved through the Model Stream Approach (Stone, T. E.; Goel, V.; Leszczak, *J. Pharmaceutical Tech.* 1994, 116-130). In this protocol, a surrogate solvent system is employed to subject the filtration device to extreme chemical conditions, which are not necessarily representative of the conditions to be of the biopharmaceutical product. The purpose for using alternative solvents is to produce a worst case scenario to indicate all the possible extractables from a given filter device. Although the Model Stream Approach provides useful information, it cannot be used to detect the actual filter extractables present in the biopharmaceutical product for human or animal use. The ability to detect filter extractables actually present in the biopharmaceutical product would assist in determining the safety and efficacy of the drug.

The present invention discloses a method that allows for detection of filter extractables in the actual biopharmaceutical product, rather that in a model solvent system. The method utilizes liquid chromatography-mass spectrometry (LCMS) to detect ions characteristic of extractables introduced by filtration of the biopharmaceutical products. Although the examples below illustrate methods of the invention for detecting filter extractables, the methods are generally applicable for any extractable that is introduced into a biopharmaceutical product during manufacturing or processing, such as plastic leachables from filter housings or other equipment having leaching potential that comes into contact with the biopharmaceutical product. Thus, the methods of the invention allow for detection of extractables, generally, in a biopharmaceutical product.

Conventional methods, such as LCUV and FTIR, are not capable of detecting extractables directly in a biopharmaceutical product either due to limited sensitivity or severe matrix interference. However, detection of extractables can now be achieved directly in the biopharmaceutical product according to the methods of this invention due to the discovery of a method and system for reducing or eliminating matrix interference. Reduction or elimination of component(s) within the biopharmaceutical product that contribute to matrix interference will allow for the detection of low or trace levels of extractables using mass spectrometry that would otherwise be masked by the interfering components. By applying the methods of the invention, detection of the filter extractables in biopharmaceutical products is now possible, and thus effectively provides an unmet need in the industry testing and reporting to the FDA.

The methods described herein are useful for detecting, identifying and optionally quantifying contaminants in a biopharmaceutical product, which may contain extractables, leachables or impurities. Extractables are compounds that can be extracted from elastomeric or plastic components of the product contacting material when in the presence of a solvent. Leachables are compounds that leach into the formulation from elastomeric or plastic components of the product contacting material. Impurities are compounds that are present in the biopharmaceutical product or can be introduced into the biopharmaceutical product. As set forth herein, the term "extractables" is intended to cover compounds that are considered leachables. For ease of discussion, the methods of the invention will be described with regard to extractables but leachables and impurities are also contemplated. The extractables are complex mixtures consisting primarily of oligomers and additives of diverse physical and chemical properties and are often present in concentrations much lower than any other ingredient of the biopharmaceutical product, making detection of their presence difficult. The FDA requires evaluation of the extractables for their impact on the safety and efficacy of the biopharmaceutical products.

Biopharmaceutical products include drug products for human or animal use. The biopharmaceutical product comprises an active pharmaceutical ingredient (API) and excipients. The API is any component that is intended to furnish pharmacological activity or other direct effect in the diagnosis, cure, mitigation, treatment, or prevention of disease, or to affect the structure or any function of the body of man or of animals. The term "API" includes those components that may undergo chemical change in the manufacture of the drug product and be present in the drug product in a modified form intended to furnish the specified activity or effect. Examples of API suitable for use with the present invention, include but is not limited to, small organic molecules, large organic molecules, nucleic acids, amino acids, and proteins. The small organic molecules typically have a molecular weight under 500 Daltons, while the large organic molecules exceed 500 Daltons. Matrix interference is often more severe when large organic molecules are present. When large organic molecules are present, it may be necessary to include a pretreatment step before the LCMS step. Representative pretreatment steps, such as precipitation, are described below.

The biopharmaceutical products can further comprise excipients, including but not limited to buffers, acids, bases, salts, solubilizers, preservatives, chelating agents, sugars, amino acids, proteins and solvents. One, several or all of these components can be present in the biopharmaceutical product. Many of these ingredients, if not all, contribute in part to matrix interference with the detectable signal of the extractables and should be eliminated or reduced from the biopharmaceutical product prior to detection of the extractables. Known methods for removing or reducing the amount of components that contribute to matrix interference can be used, such as precipitation of proteins. For examples, acetone can be added in a protein solution at the volume ratio of 4 to 1. After 15 minutes of reaction the solution will be centrifuged for 10 minutes at 15,000 RPM. The supernatant containing the analyte(s) of interests is then removed for further analysis. Methods for reducing or removing matrix interfering components can also be achieved using the novel diversion method and system described in detail below.

In the course of production, the biopharmaceutical products can extract chemical compounds from the containers or filtration devices with which they are in contact. The length of time the biopharmaceutical product is in contact, the temperature at which the contact occurs, as well as other solvents or solutes present in the biopharmaceutical product all impact the amount and type of extractable that can be present in the biopharmaceutical product. The extractables encompass one or multiple chemical species and can arise at different steps during the production of the biopharmaceutical product. For example, the extractables may be introduced by filtration when the biopharmaceutical product is passed through a filter device. Filter devices are used to remove particles and microorganisms or purify proteins from biopharmaceutical products. Representative examples include polyvinylidene fluoride (PVDF) microporous membranes and polypropylene (PP) support membranes such as the Millipore® Durapore® filter; borosilicate glass fiber microporous membranes and polypropylene support membranes such as the Millipore® Lifegard® filter; polypropylene microporous membranes and polypropylene (PP) support membranes such as the Millipore® Polygard® filter; polytetrafluoroethylene microporous membranes and polypropylene support membranes such as the Millipore® Opticap® filter; and hydrophilic polyethersulfone microporous membranes and polypropylene support membranes such as the Millipore Express® filter.

In another example, drugs can extract components of their containers during shelf-life studies, thereby becoming contaminated with extractables. Representative examples include process container films in which the fluid contact material is made of ultra low density polyethylene (ULDPE); the gas barrier is made of polyethylene vinyl alcohol copolymers (EVOH); and the outer layers are made of ethylene vinyl acetate (EVA) and ULDPE such as Millipore® PureFlex® process container film. Durapore®, Lifegard®, Polygard®, Opticap®, Millipore Express®, PureFlex® and Millipore® are registered trademarks of the Millipore Corporation, Billerica, Mass.

The method for detecting extractables in a biopharmaceutical product involves comparing the mass spectra of a test sample to a reference sample. As used herein, the "reference sample" is a sample of the biopharmaceutical product that is absent any extractables introduced during the production, but to which an extractables standard is added. For example, the reference sample can be a sample of the biopharmaceutical product that has not been filtered and to which an extractables standard is added. The extractables standard is a mixture of extractables that can be introduced into a biopharmaceutical product through the use of particular container or filter device. The extractables standard profile for a product-contacting material, such as a filter device, would be determined by previously established methods. For example, the Model Stream Approach can be applied, under a wide range of conditions (including extreme temperatures, extreme pH ranges, or reactive solvents including organic solvents, long extraction times, repetition of autoclave cycles) to a particular component of the production process, such as a filter device. The solvent of choice will be selected to mimic the solvent in the biopharmaceutical product to be tested. In many instances, water or other aqueous solvents will be the solvent of choice because most biopharmaceutical products are present in aqueous medium. Analysis of the components found during this process can indicate the chemicals that can be extracted or leached from the materials used in the production of the biopharmaceutical product and provide an extractables profile in the biopharmaceutical product. The extractables standard would contain these known components at appropriate concentrations.

As used herein, the "test sample" is a biopharmaceutical product that may contain extractables to be ascertained. For example, filtration of the biopharmaceutical product may introduce extractables, and thus would be an appropriate test sample.

Preparation previous to the injection of either the reference sample or test sample may be preformed. One possible preparation could involve heating the sample or adding sodium dodecyl sulfate (SDS) to denature and/or precipitate any proteins present. Some biopharmaceutical products may contain other ingredients that can be removed by solid-phase extraction, or alteration of the pH or ionic strength of the solution. Other sample preparation techniques can be used for the methods of this invention. One method for analyzing the concentration of the extractables in model solvents is non-volatile residue analysis. The samples may be diluted to achieve an appropriate concentration before injection into the LCMS.

Liquid chromatography is used to separate the reference and test samples independently. The mobile phases, the stationary phase, flow rate, temperature and injection volume should be optimized during the method development. Following the LC separation, the sample eluent is diverted to waste for a period of time. The diversion process removes or reduces components that can cause matrix interference, which interferes with the test method execution such that reliable data cannot be generated. Matrix interference is caused by samples with extreme pH values, high salt concentrations, reactive chemical constituents, or high concentrations of non-target compounds. The following paragraphs describe the general categories of biopharmaceutical product components that can cause matrix interference.

The Active Pharmaceutical Ingredient (API) of the biopharmaceutical product is a source of matrix interference. In some situations, the API elutes at an earlier time than the target extractable, and can be diverted away from the MS using the methods for diversion as described herein.

Another common cause of matrix interference are buffering agents. A list of possible buffering agents includes but is not limited to ACES, acetate, ADA, ammonium hydroxide, AMP (2-amino-2-methyl-1-propanol), AMPD (2-amino-2-methyl-1,3-propanediol), AMPSO, BES, BICINE, bis-tris, BIS-TRIS propane, borate, CABS, cacodylate, CAPS, CAPSO, carbonate, CHES, citrate, DIPSO, EPPS, HEPPS, ethanolamine, formate, glycine, glycylglycine, HEPBS, HEPES, HEPPSO, histidine, hydrazine, imidazole, malate, maleate, MES, methylamine, MOBS, MOPS, MOPSO, phosphate, piperazine, piperidine, PIPES, POPSO, propionate, pyridine, pyrophosphate, succinate, TABS, TAPS, TAPSO, taurine (AES), TES, tricine, triethanolamine, Trizma.

Salts are another component of a biopharmaceutical product that can introduce matrix interference into the detection. Representative salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts. Alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine are also included.

Preservatives are often added to biopharmaceutical products to lengthen the shelf live. A representative list includes ascorbic acid, benzoic acid, benzyl alcohol, benzylalkonium chloride, erythorbic acid, propionic acid, sorbic acid, thiodipropionic acid, ascorbyl palmitate, butylated hydroxyanisole, butylated hydroxytoluene, calcium ascorbate, calcium propionate, calcium sorbate, dilauryl thiodipropionate, gum guaiac, methylparaben, metabisulfite, m-cresol, paraben, potassium bisulfite, potassium metabisulfite, potassium sorbate, propyl gallate, propylparaben, sodium ascorbate, sodium benzoate, sodium bisulfite, sodium metabisulfite, sodium propionate, sodium sorbate, sodium sulfite, stannous chloride, sulfur dioxide, tocopherols In order to dissolve and maintain dissolution of the API, solubilizers can be added to the biopharmaceutical product, but these solubilizers can also cause matrix interference. PEG, Tween, CMC, and SDS are all possibilities for agents used as solubilizers.

Chelating agents can also be a source of matrix interference and include, but are not limited to, citric acid, tartaric acid, calcium acetate, calcium chloride, calcium citrate, calcium diacetate, calcium gluconate, calcium hexametaphosphate, monobasic calcium phosphate, calcium phytate, dipotassium phosphate, disodium phosphate, isopropyl citrate, malic acid, monoisopropyl citrate, potassium citrate, sodium citrate, sodium diacetate, sodium gluconate, sodium hexametaphosphate, sodium metaphosphate, sodium phosphate, sodium pyrophosphate, tetra sodium pyrophosphate, sodium tartrate, sodium potassium tartrate, sodium thiosulfate, sodium tripolyphosphate, stearyl citrate, and tetrasodium ethylenediamine tetraacetate.

Acid and bases are often added to biopharmaceutical products to adjust pH or to enhance efficacy, but their presence is a source of matrix interference. Representative acids includes nitric acid, hydrochloric acid, sulfuric acid, perchloric acid, hydrobromic acid, hydroiodic acid, acetic acid, ascorbic acid, boric acid, butanoic acid, carbonic acid, citric acid, formic acid heptanoic acid, hexanoic acid, hydrocyanic acid, hydrofluoric acid, lactic acid, nitrous acid, octanoic acid, oxalic acid, pentanoic acid, phosphoric acid, propanoic acid, sulfurous acid, and uric acid. Representative bases include lithium hydroxide, sodium hydroxide, potassium hydroxide, magnesium hydroxide, calcium hydroxide, alanine, ammonia, dimethylamine, ethylamine, glycine, hydrazine, methylamine, and trimethylamine.

Sugars, including glucose (dextrose), fructose, galactose, ribose, sucrose, lactose, maltose, trehalose, cellobiose, arabitol, erythritol, glycerol, isomalt, lactitol, maltitol, mannitol, sorbitol, and xylitol, proteins such as albumin, and peptides can all be sources of matrix interference An example of amino acid used as an excipient is L-histidine.

An example of protein used as an excipient is bovine serum albumin (BSA).

Diverting the sample eluent involves channeling the sample away from the mass spectrometer immediately after the liquid chromatography step in the method. The diversion process will continue for a pre-set amount of time, based upon previous experimental determinations. The sample should be diverted until immediately before the retention time known for the first extractables of the standard. The diversion time will depend on the components of the biopharmaceutical product being tested, the nature of the extractables likely to be present, and the type of device from which the extractables originated.

After the diversion step, the remaining reference sample is processed through a mass spectrometer to obtain a reference mass spectrum. The reference mass spectrum is the intensity vs. m/z (mass-to-charge ratio) plot for the reference sample, that is, the sample that does not contain any extractables from the production of the biopharmaceutical product. The ions found in the reference mass spectrum are due to the extractables standard added to the reference sample before injection into the LCMS.

Similarly, the remaining test sample is processed through a mass spectrometer to obtain a test mass spectrum. The test mass spectrum is an intensity vs. m/z (mass-to-charge ratio) plot for the test sample, that is, the biopharmaceutical product that has been in contact with a container or filtration device, and therefore may contain extractables. The test sample mass spectrum is compared to the reference sample mass spectrum to detect the presence or absence of the filter extractables in the test sample. The ions, if found, in the test mass spectrum are due to the extractables leached from the material during the production of the biopharmaceutical product.

The appearance of peak(s) in the LC chromatogram or mass spectrum of the sample indicates that the extractable is present. The detection of the extractables is accomplished by discovering the presence of peak(s) in either the LC chromatogram or the mass spectrum. Comparing the test mass spectrum and the reference sample mass spectrum will indicate the presence or absence of the extractables in the test sample. Peaks that appear in both the reference and test mass spectra will be taken to indicate the presence of the filter extractables in the biopharmaceutical product. Peaks that appear in only the reference mass spectrum, but not the test mass spectrum will be taken to indicate the absence of the filter extractables in the biopharmaceutical product.

Another embodiment of this method is to quantify, or determine the number of discrete filter extractables as well as the concentration at which the total extractables is present in the biopharmaceutical product. The quantification step can include measurement of peak heights in the LC chromatogram.

EXEMPLIFICATION

Example 1

Isolation and Detection of Filter Extractables

Following an autoclave cycle of 126° C. for 60 min, a 10-inch 0.22 µm Durapore® filter was extracted in Milli-Q® water for 24 h at ambient temperature. Durapore® and Milli-Q® are registered trademarks of the Millipore Corporation, Billerica, Mass. A control was prepared using Milli-Q® water without the filter under the same conditions. The solutions were then analyzed by non-volatile residue analysis, diluted 10 times using Milli-Q® water before injection into the LCMS.

Figure 3:
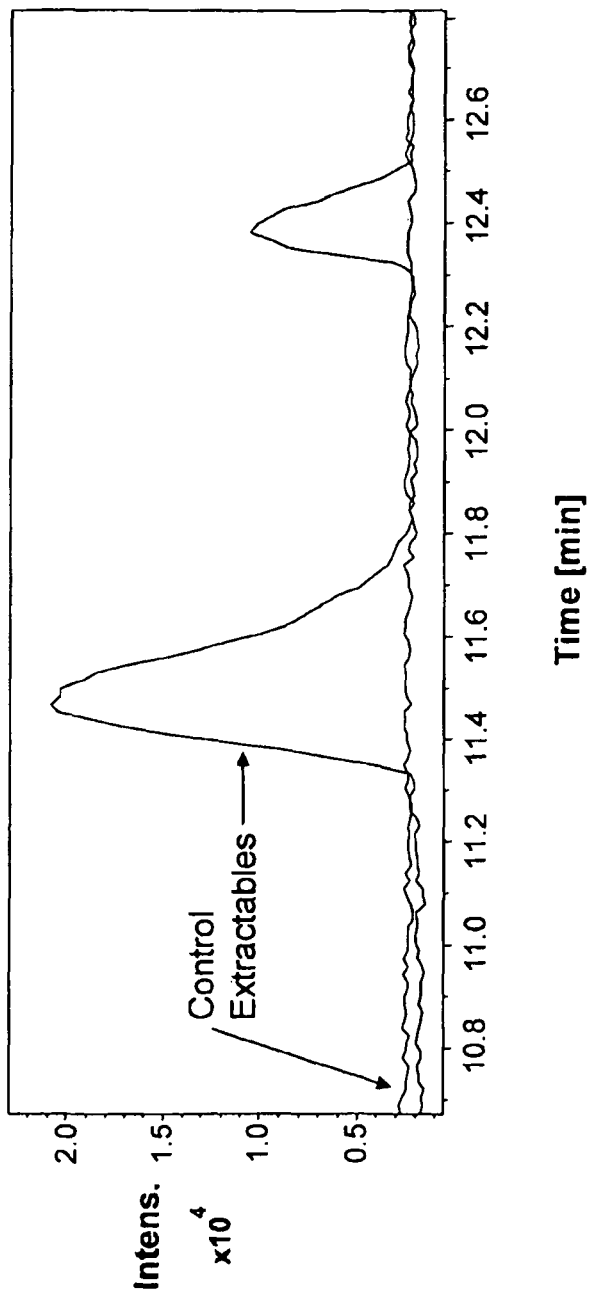
FIG. 3 is the base peak chromatogram from the liquid chromatography separation step of the filter extractables standard overlaid onto the chromatogram of the control.
Figure 4:
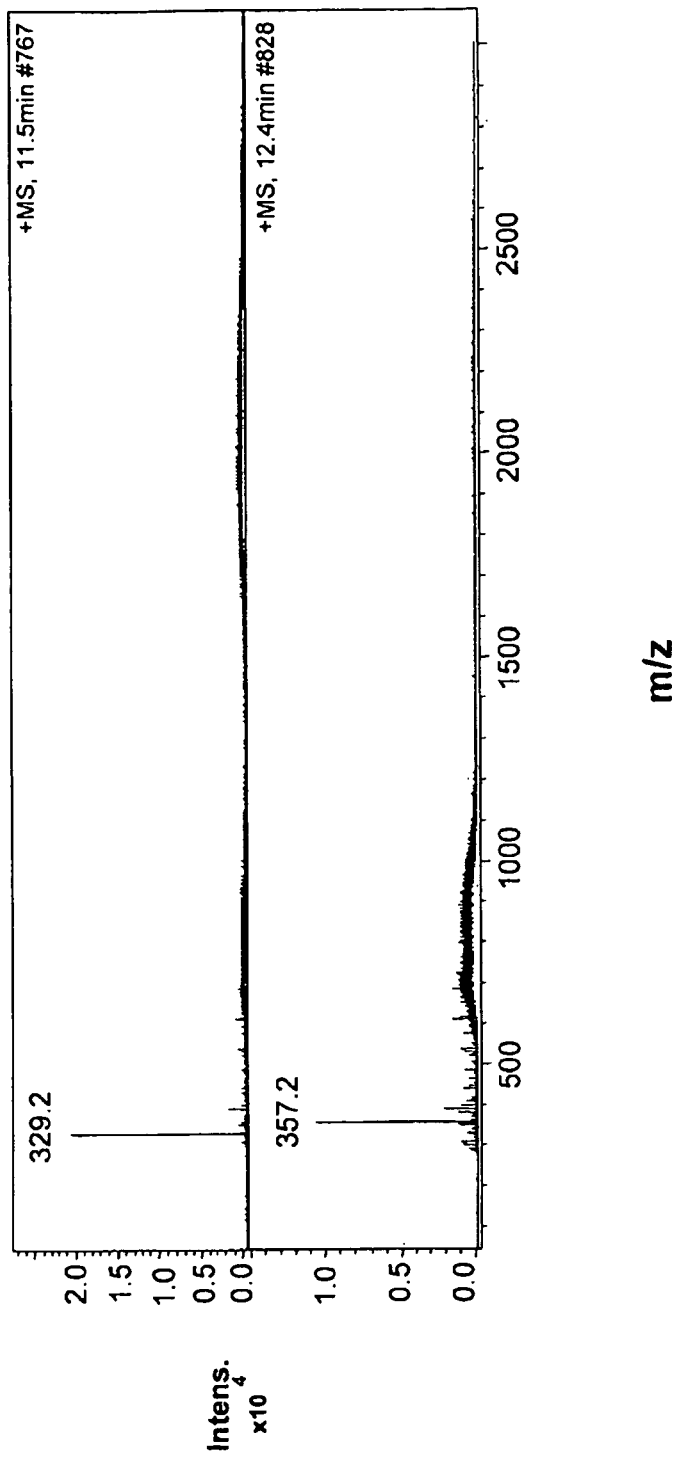
FIG. 4 is the mass spectra from the two peaks identified in the chromatogram of the liquid chromatography step of the standard.

Shown in FIG. 3 are the base peak chromatograms of the extractables and the control. When compared with the control, the extractables was found to contain two peaks characteristics to the Durapore® filter. The mass spectrum of the species responsible for the two peaks seen in the chromatogram of FIG. 3 is depicted in FIG. 4. The peaks at M/Z 329 and 357 correspond to compounds known to originate from the filter extractables. The peaks were tentatively identified as phenolic-type of antioxidants used in the membrane manufacturing process. Since these compounds exist at extremely low concentrations, LCMS provides the best mode for detection of their presence.

Example 2 and 3

Isolation and Detection of Filter Extractables in a Biopharmaceutical Product Drug products were spiked with an extractables standard at ppm levels. In the large-molecule application, amino acids or proteins are precipitated from the biopharmaceutical product, and then the sample is injected into the LCMS. At the same time, the drug products without spiking were prepared the same way before being injected.

Figure 5:
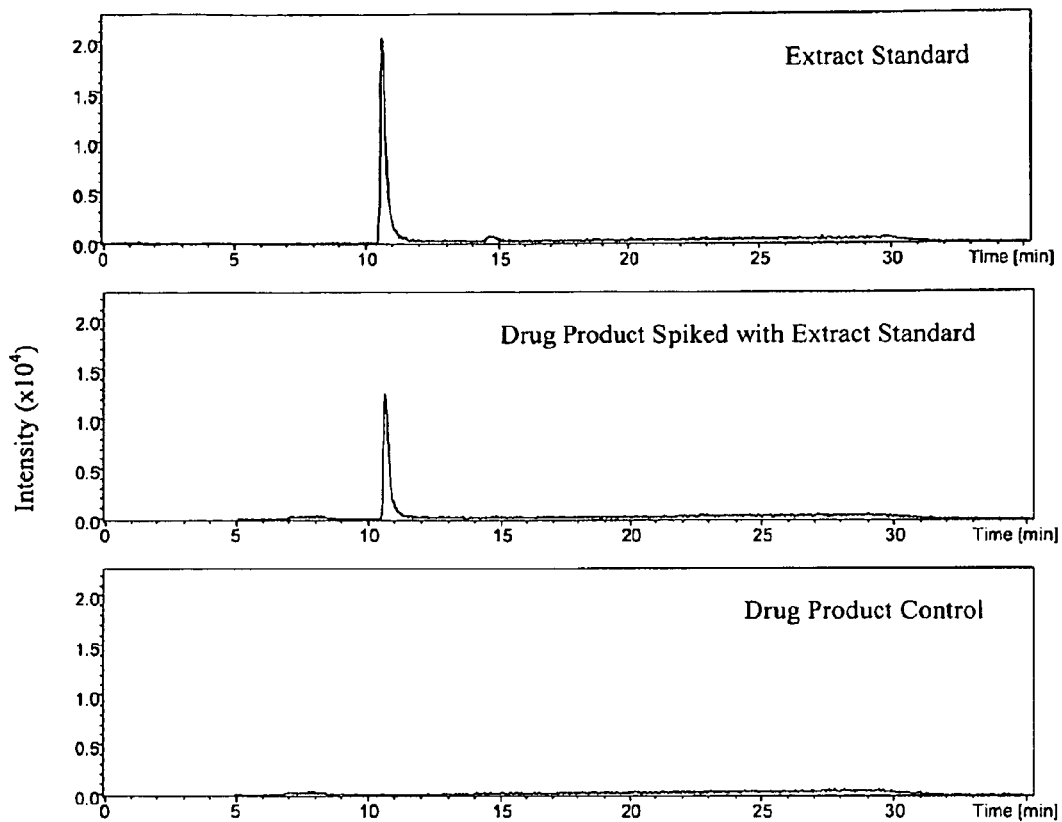
FIG. 5 is the overlay of the chromatograms of the extractables standard, a small molecule-based drug product and the small molecule-based drug product spiked with the extractables standard.
Figure 6:
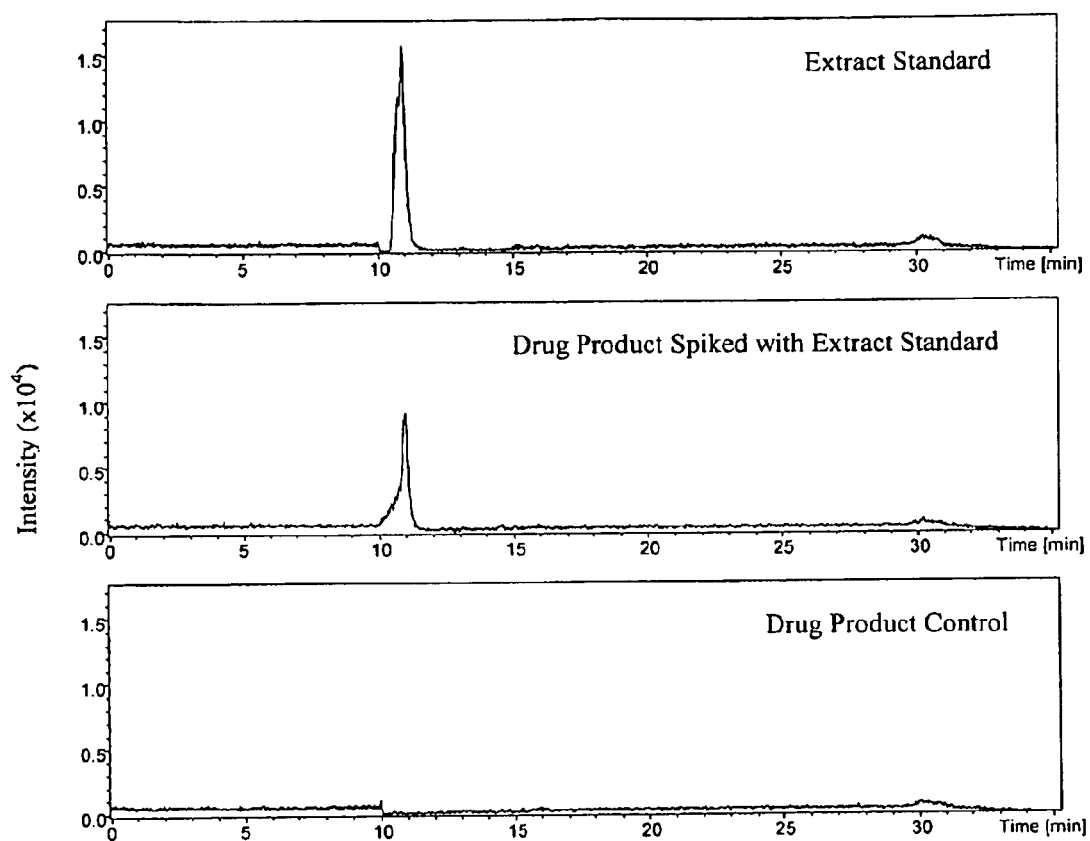
FIG. 6 is the overlay of the chromatograms of the extractables standard, a large molecule-based drug product and a large molecule-based drug product spiked with the extractables standard.

The overlay of the chromatograms of the extractables standard, a drug product and the small molecule-based drug product spiked with the extractables standard (FIG. 5: small molecule; FIG. 6: large molecule). The results demonstrated that despite matrix suppression, the extractables could be detected in the presence of the drug ingredients in the spiked samples. This method was applied to a wide range of biopharmaceutical ingredients and showed to be sensitive and robust for most applications. The method allowed for the first time verification of the presence or absence of the extractables directly in the biopharmaceutical product. In contrast, none of the conventional methods allows for such detection.

While this invention has been particularly shown and described with references to example embodiments thereof, it will be understood by those skilled in the art that various changes in form and details may be made therein without departing from the scope of the invention encompassed by the appended claims.

What is claimed is:

1. A method for reducing or eliminating matrix interfering components in a biopharmaceutical product in a liquid chromatography-mass spectrometry system to permit detection of the presence of an extractable, comprising:
    diverting to waste the entire flow of an eluant emerging from liquid chromatography of a sample comprising the biopharmaceutical product and an extractable introduced in manufacturing of the biopharmaceutical product, for a time period to reduce or remove components that cause matrix interference to a degree sufficient to allow a desired accuracy in detection of the extractable;
    directing flow of a calibrant liquid to the mass spectrometer during the time period; and
    after the time period, directing the entire flow of the eluant to the mass spectrometer to detect the presence of the extractable that was introduced in manufacturing the biopharmaceutical product.

2. A method according to claim 1, further comprising directing flow of the calibrant liquid to waste after the time period.

3. A method according to claim 1, wherein diverting the eluant to waste during the time period and directing the eluant to the mass spectrometer after the time period are performed using a six-port injection valve.

4. A method according to claim 3, comprising directing the entire flow of the eluant to a port of the six-port injection valve that is adjacent to both (i) a port from which liquid flows directly to a mass spectrometer; and (ii) a port from which liquid flows directly to waste.

5. A method according to claim 2, wherein diverting the eluant to waste during the time period and directing the eluant to the mass spectrometer after the time period are performed using a six-port injection valve.

6. A method according to claim 5, comprising directing the entire flow of the eluant to a port of the six-port injection valve that is adjacent to both (i) a port from which liquid flows directly to a mass spectrometer; and (ii) a port from which liquid flows directly to waste.

7. A method according to claim 6, wherein directing flow of the calibrant liquid to the mass spectrometer during the time period and directing flow of the calibrant liquid to waste after the time period are performed using a six-port injection valve.

8. A method according to claim 7, comprising directing flow of the calibrant liquid to the mass spectrometer during the time period by way of a flow loop between two adjacent ports of the six-port injection valve.

9. A liquid chromatography diverter for reducing or eliminating matrix interfering components in a biopharmaceutical product in a liquid chromatography-mass spectrometry system, comprising:
    an eluant input port of a six-port injection valve, the eluant input port being in a liquid flow connection with a liquid chromatogaphy column; and
    a mass spectrometer output port of the six-port injection valve, the mass spectrometer output port being in a liquid flow connection with a mass spectrometer;
    wherein the six-port injection valve is configured to be automatically switched between a waste flow configuration and a source flow configuration, the waste flow configuration diverting an entire flow from the eluant input port to be directed to waste, and the source flow configuration directing the entire flow from the eluant input port to be directed to the mass spectrometer;
    wherein the mass spectrometer output port is an adjacent port of the six-port injection valve to the eluant input port, and wherein a waste port is another adjacent port to the eluant input port, and wherein the waste flow configuration directs the entire flow from the eluant input port to waste via the waste port, and wherein the source flow configuration directs the entire flow from the eluant input port to the mass spectrometer via the mass spectrometer output port;
    the diverter further comprising a calibrant flow loop between two adjacent ports of the six-port injection valve, the waste flow configuration directing flow of a calibrant liquid through the calibrant flow loop and to the mass spectrometer, and the source flow configuration directing flow of the calibrant liquid to waste and forming a closed flow loop that includes the calibrant flow loop, wherein the calibrant flow loop is connected to its two adjacent ports to receive only the calibrant liquid and not to receive liquid from the liquid chromatography column.

* * * * *